(12) United States Patent
Rieping et al.

(10) Patent No.: US 6,689,592 B2
(45) Date of Patent: Feb. 10, 2004

(54) PROCESS FOR THE ENZYMATIC PRODUCTION OF D-PANTOTHENIC ACID AND/OR ITS SALTS

(75) Inventors: Mechthild Rieping, Bielefeld (DE); Thomas Hermann, Bielefeld (DE); Walter Pfefferle, Halle (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/052,270

(22) Filed: Jan. 23, 2002

(65) Prior Publication Data

US 2002/0137148 A1 Sep. 26, 2002

(30) Foreign Application Priority Data

Feb. 13, 2001 (DE) ......................... 101 06 460

(51) Int. Cl.$^7$ .............. C12P 1/00; C12N 9/10; C12N 9/02; C07H 21/04
(52) U.S. Cl. .............. 435/146; 435/193; 435/189; 435/41; 536/23.2
(58) Field of Search ............... 435/41, 193, 189; 536/23.2

(56) References Cited

U.S. PATENT DOCUMENTS 5,518,906 A    5/1996   Hikichi et al.

FOREIGN PATENT DOCUMENTS

| EP | 0 493 060 | 7/1992 |
| EP | 0 931 833 | 7/1999 |
| EP | 1 001 027 | 5/2000 |
| EP | 1 050 219 | 11/2000 |
| WO | WO 96/33283 | 10/1996 |
| WO | WO 01/00843 | 1/2001 |
| WO | WO 02/064806 | 8/2002 |
| WO | WO 02/072838 | 9/2002 |

OTHER PUBLICATIONS

Old et al Nucleic acid hybridization methods. In: Principles of Gene manipulation; an introduction to genetic engineering. Ed: Old and Primrose Blackwell Scientific Pubs Boston, MA. 1985 pp. 117–120.*
Ausubel et al Protein Expression In: Current Protocols in Molecular Biology. Ed: Ausubel et al John Wiley & Sons, Inc. New York 1987 Chapter 16.*
Hodges et al Use a Standard Bibliographical Form. In: Harbrace Colege Handbook. Ed: Hodges et al Harcourt Brace Jovanovic, Inc. New York 1977 pp. 413–415.*
Swope SL, Huganir RL. Molecular cloning of two abundant protein tyrosine kinases in Torpedo electric organ that associate with the acetylcholine receptor. J Biol Chem. Nov. 25, 1993;268(33):25152–61.*
Mohamed AS, Swope SL. Phosphorylation and cytoskeletal anchoring of the acetylcholine receptor by Src class protein–tyrosine kinases. Activation by rapsyn. J Biol Chem. Jul. 16, 1999;274(29):20529–39.*
K. Duncan, et al., Biochemical Journal, vol. 234, No. 1, XP–008013071, pp. 49–57, "The serC–aroA Operon of *Eschirichia coli* A Mixed Function Operon Encoding Enzymes From Two Different Amino Acid Biosynthetic Pathways", 1986.
C. Drewke, et al., FEBS Letters, vol. 390, No. 2, XP–002229152, pp. 179–182, "4–O–Phosphoryl–$_L$–Threonine, A Substrate of the pdxC(serC) Gene Product Involved in Vitamin B$_6$ Biosynthesis", 1996.

* cited by examiner

*Primary Examiner*—Rebecca E. Prouty
*Assistant Examiner*—Sheridan Swope
(74) *Attorney, Agent, or Firm*—Oblon, Spivak, McClelland, Maier & Neustadt, P.C.

(57) ABSTRACT

A process for the enzymatic production of D-pantothenic acid and/or its salts or feedstuffs additives containing the latter by fermentation of microorganisms of the family Enterobacteriaceae, in particular those that already produce D-pantothenic acid, wherein the nucleotide sequence(s) coding for the serC gene is/are enhanced, in particular overexpressed, in the microorganisms.

11 Claims, 1 Drawing Sheet

US 6,689,592 B2

PROCESS FOR THE ENZYMATIC PRODUCTION OF D-PANTOTHENIC ACID AND/OR ITS SALTS

BACKGROUND OF THE INVENTION

1. Field of the Invention

The present invention relates to a process for the enzymatic production of D-pantothenic acid and/or its salts or mixtures containing the same, using microorganisms of the family Enterobacteriaceae in which at least the serC gene is enhanced.

2. Description of the Background

Several thousands of tons of pantothenic are produced worldwide each year. Pantothenic acid is used among other things in human medicine, in the pharmaceutical industry and in the food industry. A large part of the pantothenic acid that is produced is used as an animal feedstuff for commercially important animals such as poultry and pigs. The worldwide demand for pantothenic acid is rising.

Pantothenic acid may be produced by chemical synthesis or biotechnologically by fermenting suitable microorganisms in suitable nutrient solutions. In the chemical synthesis DL-pantolactone is an important precursor. DL-pantolactone is produced in a multi-stage process from formaldehyde, isobutyl aldehyde and cyanide, in which in further process steps the racemic mixture is separated and the D-panto-lactone is condensed with β-alanine to produce the desired D-pantothenic acid.

The typical commercial form is the calcium salt of D-pantothenic acid. The calcium salt of the racemic mixture of D,L-pantothenic acid is also commonly used.

The advantage of the enzymatic production by microorganisms is the direct formation of the desired stereoisomer form, namely the D-form, which is free of L-pantothenic acid.

Various species of bacteria, such as for example *Escherichia coli* (*E. coli*), *Arthrobacter ureafaciens*, *Corynebacterium erythrogenes*, *Brevibacterium ammoniagenes* and also yeasts, such as for example *Debaromyces castellii*, can produce D-pantothenic acid in a nutrient solution containing glucose, DL-pantoic acid and β-alanine, as demonstrated in EP-A 0 493 060. EP-A 0 493 060 furthermore shows that with *E. coli* the formation of D-pantothenic acid in a nutrient solution containing glucose, DL-pantoic acid and β-alanine is improved by amplification of pantothenic acid biosynthesis genes from *E. coli* that are contained on the plasmids pFV3 and pFV5.

EP-A 0 590 857 and U.S. Pat. No. 5,518,906 describe mutants derived from *E. coli* strain IF03547, such as FV5714, FV525, FV814, FV521, FV221, FV6051 and FV5069, that exhibit resistance to various antimetabolites such as salicylic acid, a-ketobutyric acid, β-hydroxyaspartic acid, O-methyl-threonine and α-ketoisovaleric acid. These mutants produce pantoic acid in a nutrient solution containing glucose, and produce D-pantothenic acid in a nutrient solution containing glucose and β-alanine. EP-A 0 590 857 and U.S. Pat. No. 5,518,906 also show that, after amplification of the pantothenic acid biosynthesis genes panB, panC and panD that are said to be contained on the plasmid pFV31, in the aforementioned strains the production of D-pantoic acid is improved in glucose-containing nutrient solutions, while the production of D-pantothenic acid is improved in a nutrient solution that contains glucose and β-alanine.

Furthermore, the promoting action of the enhancement of the ilvGM operon on the production of D-pantothenic acid is reported in WO 97/10340. Finally, the effect of the enhancement of the panE gene on the formation of D-pantothenic acid is reported in EP-A-1001027.

According to known methos, D-pantothenic acid or the corresponding salt is isolated from the fermentation broth and purified (EP-A-0590857 and WO 96/33283) and consequently used in purified form, or the fermentation broth containing D-pantothenic acid is dried as a whole (EP-A-1050219) and used in particular as a feedstuffs additive.

In view of the increasing demand for D-pantothenic acid, there remains a need for new methods for producing this material.

SUMMARY OF THE INVENTION

It is an object of the present invention to provide new methods for the improved enzymatic production of D-pantothenic acid and/or its salts and/or feedstuffs additives containing the same.

The invention provides a method for the production of D-pantothenic acid and/or its salts or in addition to the latter the production of feedstuffs additives containing further constituents from the fermentation, by fermentation of microorganisms of the family Enterobacteriaceae, in particular those that already produce D-pantothenic acid, in which a) the nucleotide sequence(s) in the microorganisms coding for the endogenous serC gene is amplified, in particular overexpressed, in conditions that are suitable for the production of 3-phosphoserine aminotransferase, b) the D-pantothenic acid and/or its salts are enriched in the medium or in the cells of the microorganisms, and c) the desired products are isolated after the end of the fermentation, the biomass and/or optionally further constituents of the fermentation broth being separated in an amount of 0 to 100%, wherein the microorganisms produce D-pantothenic acid.

The invention also provides a process in which after the end of the fermentation the biomass remains partially or totally in the fermentation broth and the broth obtained in this way is worked up, optionally after concentration, to form a mixture containing solid D-pantothenic acid and/or its salts, which preferably contains further constituents of the fermentation broth.

Accordingly, the present invention provides a method of producing D-pantothenic acid and/or a salt thereof, comprising:

fermenting a microorganism of the family Enterobacteriaceae, in which the nucleotide sequence (s) in the microorganism coding for the endogenous serC gene is amplified, in a medium under conditions suitable for the production of 3-phosphoserine aminotransferase, wherein the microorganism produces the D-pantothenic acid and/or a salt thereof.

The present invention also provides a method of producing a feedstuffs additive, comprising:

producing D-pantothenic acid and/or a salt thereof as described above, and combining the D-pantothenic acid and/or a salt thereof with a carrier suitable for use in feedstuffs.

The present invention also provides a vector for the expression of the serC gene from *E. coli*, containing a promoter and the gene sequence.

The present invention also provides a microorganism of the family Enterobacteriaceae, transformed with the vector described above.

The present invention also provides a method of producing D-pantothenic acid and/or a salt thereof by fermentation of the microorganism described above.

The present invention also provides a method of producing a foodstuffs additive, comprising:

(a) producing D-pantothenic acid or a salt thereof as described above, wherein the alkaline earth metal of the alkaline earth salt is magnesium and/or calcium, (a) optionally, removing water from the fermentation broth, (b) separating the biomass formed during the fermentation is separated in an amount of 0 to 100%, (c) optionally, adding one or more magnesium and/or calcium salts of D-pantothenic acid to the fermentation broths from (b), and (d) producing the feedstuffs additive, wherein the amount of the added one or more magnesium and/or calcium salts of D-pantothenic acid is such that the amount of in the feedstuffs additive is in the range from about 20 to 80 wt. % based on the dry mass of the feedstuffs additive.

A more complete appreciation of the invention and many of the attendant advantages thereof will be readily obtained as the same becomes better understood by reference to the following FIGURE in conjunction with the detailed description below.

Figure 1:
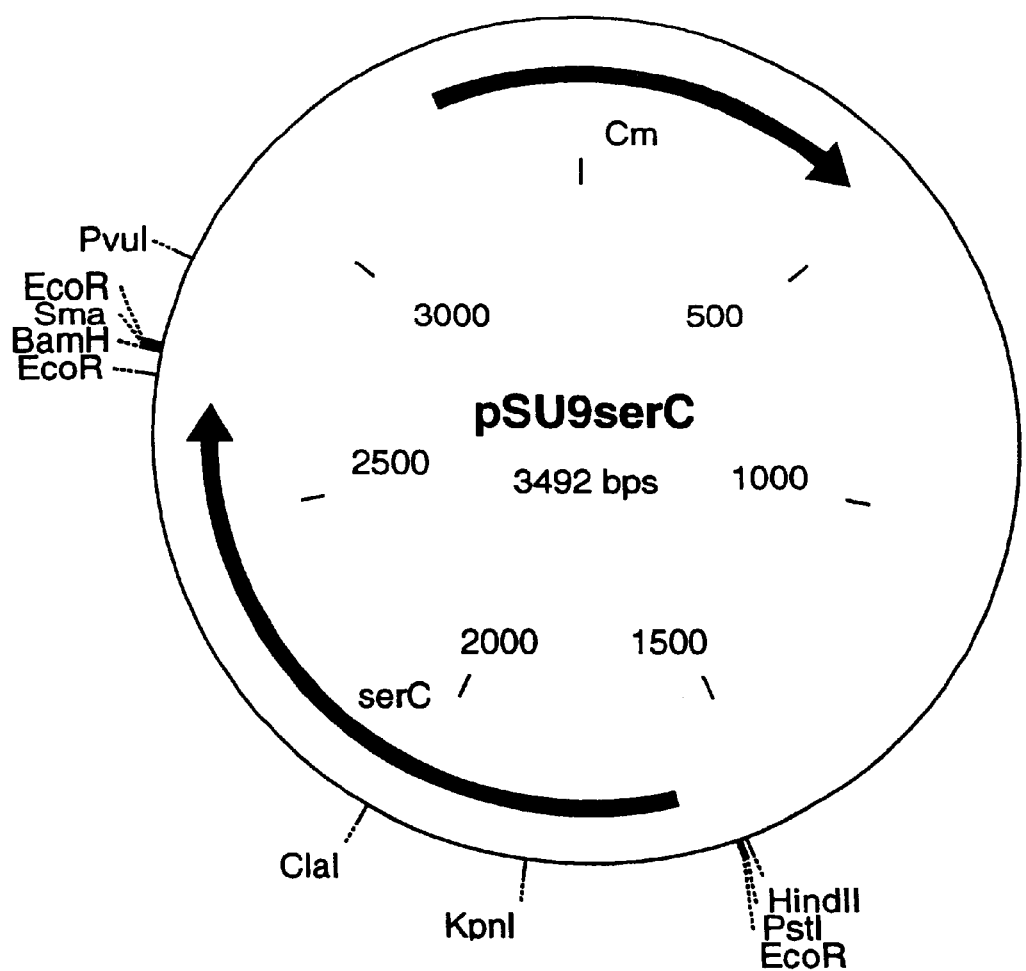
FIG. 1: Map of the plasmid pSU9serC containing the serC gene

Length details are as approximate. The abbreviations and designations employed have the following meanings:

Cm: chloramphenicol resistance gene serC: coding region of the serC gene

The abbreviations for the restriction enzymes have the following meanings

BamHI: restriction endonuclease from *Bacillus amyloliquefaciens*

ClaI: restriction endonuclease from *Caryphanon latum*

EcoRI: restriction endonuclease from *Escherichia coli*

HindIII: restriction endonuclease from *Haemophilus influenzae*

KpnI: restriction endonuclease from *Klebsiella pneumoniae*

PstI: restriction endonuclease from *Providencia stuartii*

PvuI: restriction endonuclease from *Proteus vulgaris*

SmaI: restriction endonuclease from *Serratia marcescens*

DETAILED DESCRIPTION OF THE INVENTION

Where the terms "D-pantothenic acid" or "pantothenic acid" or "pantothenate" are used hereinafter, this is understood to refer not only to the free acids but also to the salts of D-pantothenic acid such as, for example, the calcium, sodium, ammonium or potassium salt.

The term "enhancement" describes in the present invention the raising of the intracellular activity of one or more enzymes and/or proteins in a microorganism that are coded by the corresponding DNA, by for example increasing the number of copies of the gene or genes, using a strong promoter or a gene or allele that codes for a corresponding enzyme and/or protein having a high activity, and optionally combining these measures.

By these enhancement measures, in particular overexpression, the activity or concentration of the corresponding protein is generally raised by at least 10%, 25%, 50%, 75%, 100%, 150%, 200%, 300%, 400% or 500%, and at most up to 1000% or 2000% with respect to that of the wild type protein or with respect to the activity or concentration of the protein in the starting microorganism.

The microorganisms that are provided by the present invention can produce D-pantothenic acid from glucose, sucrose, lactose, fructose, maltose, molasses, starch, cellulose or from glycerol and ethanol. The microorganisms are members of the Enterobacteriaceae family, in particular of the genus Escherichia. Among the genus Escherichia the species *Escherichia coli* is especially preferred. Within the species *Escherichia coli*, the so-called K-12 strains, such as for example the strains MG1655 or W3110 (Neidhard et al.: *Escherichia coli* and Salmonella. Cellular and Molecular Biology (ASM Press, Washington D.C.)) or the *Escherichia coli* wild type strain IF03547 (Institute for Fermentation, Osaka, Japan) and mutants derived therefrom are suitable and are able to produce D-pantothenic acid.

Suitable strains of the genus Escherichia that produce D-pantothenic acid, in particular of the species *Escherichia coli*, include for example

*Escherichia coli* FV5069/pFV31

*Escherichia coli* FV5069/pFV202

*Escherichia coli* FE6/pFE80 and

*Escherichia coli* KE3

It has been found that Enterobacteriaceae, after enhancement and in particular overexpression of the serC gene coding for 3-phosphoserine aminotransferase, produce D-pantothenic acid in an improved way.

The nucleotide sequence of the serC gene of *Escherichia coli* has been published by Duncan and Coggins (Biochemical Journal 234(1):49–57 (1986)) and can also be obtained from the genome sequence of *Escherichia coli* published by Blattner et al. (Science 277, 1453–1462 (1997)) under Accession Number AE000193.

The serC genes described in the publications cited above may also be used in the present invention. In addition alleles of the serC gene may be used that are produced as a result of the degeneracy of the genetic code or by functionally neutral sense mutations.

In order to achieve an overexpression the number of copies of the corresponding genes can be increased, or alternatively the promoter and regulation region or the ribosome binding site that is located upstream of the structure gene may be mutated. Expression cassettes that are incorporated upstream of the structure gene act in the same way. By means of inducible promoters it is in addition possible to raise the expression during the course of the enzymatic production of D-pantothenic acid. The expression is also improved by measures aimed at extending the lifetime of the m-RNA. Furthermore the enzyme activity is also enhanced by preventing the breakdown of the enzyme protein. The genes or gene constructs may either be present in plasmids having different numbers of copies, or may be integrated and amplified in the chromosome. Alternatively, an overexpression of the relevant genes may furthermore be achieved by altering the media composition and culture conditions.

One skilled in the art will find details of the above in, inter alia, Chang and Cohen (Journal of Bacteriology 134:1141–1156 (1978)), in Hartley and Gregori (Gene 13:347–353 (1981)), in Amann and Brosius (Gene 40:183–190 (1985)), in de Broer et al. (Proceedings of the National [sic] of Sciences of the United States of America 80:21–25 (1983)), in LaVallie et al. (BIO/TECHNOLOGY 11, 187–193 (1993)), in PCT/US97/13359, in Llosa et al. (Plasmid 26:222–224 (1991)), in Quandt and Klipp (Gene 80:161–169 (1989)), in Hamilton (Journal of Bacteriology 171:4617–4622 (1989), in Jensen and Hammer (Biotechnology and Bioengineering 58, 191–195 (1998) and in known textbooks on genetics and molecular biology.

Plasmid vectors replicable in Enterobacteriaceae, such as for example cloning vectors derived from pACYC184 (Bartolomé et al.; Gene 102, 75–78 (1991)), pTrc99A (Amann et al.; Gene 69:301–315 (1988)) or pSC101 derivatives (Vocke and Bastia, Proceedings of the National Academy of Science USA 80 (21):6557–6561 (1983)) may be used. In a process according to the invention a strain transformed with a plasmid vector may be used, the plasmid vector carrying at least the nucleotide sequence coding for the serC gene.

Furthermore it may be advantageous for the production of D-pantothenic acid using strains of the family Enterobacteriaceae, in addition to the enhancement of the endogenous serC gene also to enhance, in particular to overexpress, separately or together, one or more endogenous genes selected from the following group:

the ilvGM operon (WO 97/10340) coding for acetohydroxy acid synthase II, the panB gene (U.S. Pat. No. 5,518,906) coding for ketopantoate hydroxymethyl transferase, the panE gene (EP-A-1001027) coding for ketopantoate reductase, the panD gene (U.S. Pat. No. 5,518,906) coding for aspartate decarboxylase, the panC gene (U.S. Pat. No. 5,518,906) coding for pantothenate synthetase, the glyA gene (Plamann et al (Nucleic Acids Research 11(7):2065–2075(1983)) coding for serine hydroxymethyl transferase, and the genes gcvt, gcvH and gcvP coding for the glycine cleavage system (Okamura-Ikeda et al., European Journal of Biochemistry 216, 539–548 (1993)).

Finally, it may be advantageous for the production of D-pantothenic acid using strains of the family Enterobacteriaceae, in addition to enhancing of the serC gene, also to attenuate, in particular to switch off or to express at a low level, the following gene the avtA gene (EP-A-1001027) coding for transaminase C.

The term "attenuation" describes in this connection the reduction or switching off of the intracellular activity of one or more enzymes (proteins) in a microorganism that are coded by the corresponding DNA, by for example using a weak promoter or using a gene or allele that codes for a corresponding enzyme (protein) having a low activity and/or inactivating the corresponding gene or enzyme (protein), and optionally combining these measure.

By means of these attenuation measure the activity or concentration of the corresponding protein is in general reduced to 0 to 75%, 0 to 50%, 0 to 25%, 0 to 10% or 0 to 5% of the activity or concentration of the wild type protein, and/or the activity or concentration of the protein in the starting microorganism.

Furthermore it may be advantageous for the production of D-pantothenic acid, in addition to the overexpression of the serC gene, also to switch off undesirable secondary reactions (Nakayama: Breeding of Amino Acid Producing Microorganisms, in:

Overproduction of Microbial Products, Krumphanzl, Sikyta, Vanek (Eds.), Academic Press, London, UK, 1982). In the process according to the invention bacteria may be used in which the metabolic pathways that reduce the formation of D-pantothenic acid are at least partially switched off.

The microorganisms produced according to the invention may be cultivated in a batch process, in a fed batch process, or in a repeated fed batch process. A summary of known cultivation methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium to be used must satisfy in an appropriate manner the requirements of the respective strains. Descriptions of culture media for various microorganisms are contained in the textbook Manual of Methods for General Bacteriology of the American Society for Bacteriology (Washington D.C., USA, 1981). As carbon source there may be used sugars and carbohydrates such as for example glucose, sucrose, lactose, fructose, maltose, molasses, starch and cellulose, oils and fats such as for example soya bean oil, sunflower oil, groundnut oil and coconut oil, fatty acids such as for example palmitic acid, stearic acid and linoleic acid, alcohols such as for example glycerol and ethanol, and organic acids such as for example acetic acid. These substances may be used individually or as a mixture.

As nitrogen source there may be used organic nitrogen-containing compounds such as peptones, yeast extract, meat extract, malt extract, corn steep liquor, soy bean flour and urea, or inorganic compounds such as ammonium sulfate, ammonium chloride, ammonium phosphate, ammonium carbonate and ammonium nitrate. The nitrogen sources may be used individually or as a mixture.

As phosphorus source there may be used phosphoric acid, potassium dihydrogen phosphate or dipotassium hydrogen phosphate or the corresponding sodium-containing salts.

The culture medium must furthermore contain salts of metals, such as for example magnesium sulfate or iron sulfate, that are necessary for growth. Finally, essential growth promoters such as amino acids and vitamins may be used in addition to the aforementioned substances. Moreover, precursors of D-pantothenic acid such as aspartate, β-alanine, ketoisovalerate, ketopantoic acid or pantoic acid and optionally their salts may be added to the culture medium. The aforementioned starting substances may be added to the culture in the form of a single batch or may be metered in a suitable way during the cultivation.

In order to control the pH of the culture basic compounds such as sodium hydroxide, potassium hydroxide, ammonia or ammonia water, or acidic compounds such as phosphoric acid or sulfuric acid are used in an appropriate way.

It is likewise possible to add, for the formation of the alkaline earth salts of pantothenic acid, in particular the calcium salt, a suspension or solution of an alkaline earth-containing inorganic compound such as for example calcium hydroxide or an organic compound such as the alkaline earth salt of an organic acid, for example calcium acetate, continuously or batchwise during the fermentation. In this way the cation necessary for the formation of the desired alkaline earth salt of D-pantothenic acid is introduced directly in the desired amount to the fermentation broth, in general in a ratio of 0.8:1 to 1.2:1, referred to pantothenic acid, preferably in stoichiometric amounts.

In order to control foam formation antifoaming agents such as for example fatty acid polyglycol esters may be used. In order to maintain the stability of plasmids suitable selectively acting substances, for example antibiotics, may be added to the medium. In order to maintain aerobic conditions oxygen or oxygen-containing gas mixtures such as for example air are introduced into the culture. The temperature of the culture is normally 25° C. to 45° C. and preferably 30° C. to 40° C. The culture is continued until a maximum amount of D-pantothenic acid has been formed. This target is normally achieved within 10 hours to 160 hours.

The D-pantothenic acid and/or the corresponding salts of D-pantothenic acid contained in the fermentation broth may then be isolated and purified according to known procedures.

It is also possible to free the D-pantothenic acid and/or fermentation broths containing its salts preferably first of all, completely or partially ($\geq 0$ to 100%), from the biomass by known separation methods such as for example centrifugation, filtration, decanting or a combination thereof. It is however also possible to allow the biomass to remain completely in the fermentation broth. In general the suspension or solution is preferably concentrated and worked up into a powder, for example by using a spray drier or a freeze-drying apparatus. This powder is then in general converted by suitable compacting or granulation processes, for example also by build-up granulation, into a coarse grain, readily flowable, storable and largely dust-free product having a grain size distribution of 20 to 2000 m, in particular 100 to 1400 m. In the granulation or compaction it is advantageous to use conventional organic or inorganic auxiliary substances, for example carriers such as starch, gelatins, cellulose derivatives or similar substances such as are normally used in foodstuffs or feedstuffs processing, as binders, gelling agents or thickening agents, or to use further substances such as for example silicic acids, silicates or stearates.

Alternatively the fermentation product with or without further of the conventional constituents of the fermentation broth may be applied to an organic or inorganic carrier material known and conventionally used in feedstuffs processing, such as for example silicic acids, silicates, grist, bran, flour, starches, sugars or other suitable materials, and/or stabilized with conventional thickening agents and binders. Examples of use and processes relating thereto are described in the literature (Die Mühle+Mischfuttertechnik 132 (1995) 49, page 817).

Optionally D-pantothenic acid and/or the desired salt of D-pantothenic acid or a preparation containing these compounds is added to the product in a suitable process stage in order to obtain and/or adjust the desired content of pantothenic acid or the desired salt.

The desired content is generally in the range from 20 to 80 wt. % (dry mass). This range includes all specific values and subranges therebetween, such as 30, 40, 50, 60, and 70 wt. % (dry mass).

The concentration of pantothenic acid may be determined by known chemical processes (Velisek; Chromatographic Science 60, 515–560 (1992)) or microbiological 30 processes, such as for example the *Lactobacillus plantarum* Test (DIFCO MANUAL, 10th Edition, pp. 1100–1102; Michigan, USA).

A pure culture of the following microorganism was filed according to the Budapest Convention on Sep. 8, 2000 at the German Collection for Microorganisms and Cell Cultures (DSMZ, Brunswick, Germany):

*Escherichia coli* K12 strain FE6-1 as DSM 13721.

EXAMPLES

Having generally described this invention, a further understanding can be obtained by reference to certain specific examples which are provided herein for the purposes of illustration only and are not intended to be limiting unless otherwise specified.

The employed minimal (M9) and full media (LB) for *Escherichia coli* are described by J. H. Miller (A short course in bacterial genetics (1992), Cold Spring Harbor Laboratory Press). The isolation of plasmid DNA from *Escherichia coli* as well as all techniques for the restriction, Klenow treatment and alkaline phosphatase treatment are carried out according to Sambrook et al. (Molecular cloning—A laboratory manual (1989) Cold Spring Harbor Laboratory Press). The transformation of *Escherichia coli* is, unless otherwise specified, carried out according to Chung et al. (Proceedings of the National Academy of Sciences of the United States of America USA (1989) 86: 2172–2175).

Example 1

Construction of the Expression Plasmid pSU9serC

The serC gene from *E. coli* K12 is amplified using the polymerase chain reaction (PCR) as well as synthetic oligonucleotides. PCR primers are synthesised starting from the nucleotide sequence of the serC gene in *E. coli* K12 MG1655 (Accession Number AE000193, Blattner et al. (Science 277, 1453–1462 (1997)) (MWG Biotech, Ebersberg, Germany):

serC1: 5'-CAACGTGGTGAGGAGAAATG-3' serC2: 5'-CTGGCTGTGGGGATTAAGCA-3'

The chromosomal *E. coli* K12 MG1655 DNA used for the PCR is isolated according to the manufacturer's instructions using Qiagen Genomic-tips 100/G (QIAGEN, Hilden, Germany). An approximately 1100 bp long DNA fragment can be amplified with the specific primers under standard PCR conditions (Innis et al. (1990) PCR Protocols. A guide to methods and applications, Academic Press) with Pfu-DNA polymerase (Promega Corporation, Madison, USA). The PCR product is ligated according to the manufacturer's instructions with the vector pCR-Blunt II-TOPO (Zero Blunt TOPO PCR Cloning Kit, Invitrogen, Groningen, Netherlands) and transformed into the *E. coli* strain TOP 10. The selection of plasmid-carrying cells is carried out on LB agar, to which 50 g/ml kanamycin has been added. After the plasmid DNA isolation the vector pCR-Blunt II-TOPOserC is cleaved with the restriction enzymes PstI and BamHI and the serC fragment is isolated using the QlAquick Gel Extraction Kit (QIAGEN, Hilden, Germany) after separation in 0.8% agarose gel. The vector pSU9 (Bartolomé et al.; Gene 102, 75–78 (1991)) is cleaved with the enzymes PstI and BamHl and ligated with the isolated serC fragment. The *E. coli* strain XL1-Blue MRF' (Stratagene, La Jolla, USA) is transformed with the ligation batch and plasmid-carrying cells are selected on LB agar to which 20 g/ml of chloramphenicol has been added. The successful cloning may be detected after the plasmid DNA isolation, by check cleavage with the enzyme NcoI. The plasmid is designated pSU9serC (FIG. 1).

Example 2

Production of the Strain FE6-1/pSU9serC

The *E. coli* strain FE6 is a valine-resistant mutant of *E. coli* K12 MG1655 (U.S. Pat. No. 6,171,845) and has been filed as DSM12379 at the German Collection for Microorganisms and Cell Cultures (DSMZ, Brunswick, Germany). Starting from FE6, spontaneous mutants are isolated after incubation at 37 C. on minimal agar to which 2 g/L of glucose and 1 g/L of β-hydroxyaspartic acid have been added. A selected individual colony resistant to β-hydroxyasparatic acid is then incubated at 37 C. on minimal agar containing 2 g/L of glucose and 0.2 g/L of O-methylthreonine. After this step a mutant designated as FE6-1 is resistant to valine, α-ketoisovaleric acid, β-hydroxyaspartic acid and O-methyl-threonine. The plasmid pSU9serC is transformed into the strain FE6-1 and plasmid-carrying cells are selected on LB agar to which 20 μg/ml of chloramphenicol have been added. The strain obtained is designated as FE6-1/pSU9serC.

Example 3

Production of the Strain FE6-1/pSU9serC,pFV31

The *E. coli* strain FV5069/pFV31 producing D-pantothenic acid is described in EP-A-0590857 and has been filed as FERM BP 4395 according to the Budapest Convention. The plasmid pFV31 is isolated from FV5069/pFV31. The *E. coli* strain FE6-1 and the strain FE6-1/pSU9serC described in Example 2 are transformed with pFV31 and plasmid-carrying cells are selected on LB agar to which 50 g/ml of ampicillin, or 50 g/ml of ampicillin and 20 g/ml of chloramphenicol have been added. The strains obtained in this way are designated as FE6-1/pFV31 and FE6-1/pSU9serC,pFV31.

Example 4

Production of D-pantothenic Acid with Strains Derived from FE6-1

The pantothenate production by the *E. coli* strains FE6-1, FE6-1/pSU9serC, FE6-1/pFV31, FE6-1/pSU9serC, pFV31 is checked in batch cultures of 10 ml contained in 100 ml Erlenmeyer flasks. For this purpose 10 ml of preculture medium of the following composition: 2 g/l yeast extract, 10 g/l $(NH_4)_2SO_4$, 1 g/l $KH_2PO_4$, 0.5 g/l $MgSO_4$ $7H_2O$ 15 g/l $CaCO_3$, and 20 g/l of glucose, is inoculated with an individual colony and incubated for 20 hours at 33° C. and 200 rpm in an ESR incubator from Kühner AG (Birsfelden, Switzerland). 200 l portions of this preculture are reinoculated in 10 ml of production medium (25 g/l $(NH_4)_2SO_4$, 2 g/l $KH_2PO_4$, 1 g/l $MgSO_4·7H_2O$, 0.03 g/l $FeSO_4·7H_2O$, 0.018 g/l $MnSO_4$ $1H_2O$, 30 g/l $CaCO_3$, 20 g/l glucose, 20 g/l βalanine and 250 mg/l thiamine) and incubated for 48 hours at 37C. In the incubation of FE6-1/pSU9serC$_{20}$ mg/l of chloramphenicol are additionally added to the medium, in the incubation of FE6-1/pFV31 50 mg/l of ampicillin are additionally added, and in the incubation of FE6-1/pSU9serC,pFV31 50 mg/l of ampicillin and 20 mg/l of chloramphenicol are additionally added. After the incubation the optical density (OD) of the culture suspension is measured with an LP2W photometer from the Dr. Lange company (Düsseldorf, Germany) at a measurement wavelength of 660 nm.

The concentration of the formed D-pantothenate is then determined in the sterile filtered culture supernatant by means of the *Lactobacillus plantarum* ATCC8014 pantothenate assays according to the manufacturer's instruction (DIFCO Company, DIFCO MANUAL, 10thEdition, pp. 1100–1102; Michigan, USA). The hydrated calcium salt of D(+)pantothenic acid (catalogue no. 25,972-1, Sigma-Aldrich, Deisenhofen, Germany)is used for the calibration.

The results of the experiment are shown in Table 1.

TABLE 1

| Strain | OD (660 nm) | Pantothenate mg/l |
| --- | --- | --- |
| FE6-1 | 10.6 | 19 |
| FE6-1/pSU9serC | 9.1 | 23 |
| FE6-1/pFV31 | 11.6 | 82 |
| FE6-1/pSU9serC, pFV31 | 11.7 | 110 |

The publications cited above are incorporated herein by reference.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 06 460.8, filed on Feb. 13, 2001, which is incorporated herein by reference.

What is claimed is:

1. A method of producing D-pantothenic acid and/or a salt thereof, comprising:
   fermenting a microorganism of the family Enterobacteriaceae, in which at least one nucleotide sequence encoding the endogenous serC gene is amplified, in a medium under conditions suitable for the production of 3-phosphoserine aminotransferase, wherein the microorganism is *Escherichia coli* and produces the D-pantothenic acid and/or a salt thereof; and
   collecting the D-pantothenic acid, or salt thereof, which is produced.

2. The method of claim 1, wherein the endogenous serC gene is overexpressed.

3. The method of claim 1, further comprising isolating at least a portion of the D-pantothenic acid and/or a salt thereof from the medium.

4. The method of claim 1, further comprising isolating at least a portion of the biomass from the medium.

5. The method of claim 1, wherein the fermentation is carried out in the presence of an alkaline earth salt, which is added continuously or batchwise to the medium, and a product containing an alkaline earth salt of D-pantothenic acid is obtained.

6. The method of claim 1, wherein one or more of the endogenous genes selected from the group consisting of
   the ilvGM operon coding for acetohydroxy acid synthase II,
   the panB gene coding for ketopantoate hydroxy-methyl transferase,
   the panE gene coding for ketopantoate reductase,
   the panD gene coding for aspartate decarboxylase, and
   the panC gene coding for pantothenate synthetase,
are amplified in the microorganism.

7. The method of claim 1 wherein the microorganism is further modified such that expression of the avtA gene is attenuated.

8. The method of claim 1, wherein the activity or concentration of the serC gene product is increased by 10–2000% with respect to that of the starting microorganism.

9. The method of claim 6, wherein transformed stains are used in which a serC gene is present integrated in plasmids or in the chromosome and is amplified.

10. A method of producing D-pantothenic acid and/or a salt thereof by:
 fermenting a microorganism of the family Enterobacteriaceae transformed with a vector for the expression of the serC gene from *E. coli,* said vector containing a promoter and the gene sequence; and
 collecting the D-pantothenic acid, or salt thereof, which is produced.

11. A method of producing D-pantothenic acid and/or a salt thereof by fermentation of a microorganism of the family Enterobacteriaceae, transformed with a plasmid pSU9serC.

* * * * *